United States Patent [19]

Davis

[11] 4,134,395

[45] Jan. 16, 1979

[54] METHOD OF USING MAGNETIC FIELDS TO CONDUCT A SCREENING DIAGNOSTIC EXAMINATION

[75] Inventor: Albert R. Davis, Green Cove Springs, Fla.

[73] Assignee: Biomagnetics International, Inc., Jacksonville, Fla.

[21] Appl. No.: 755,340

[22] Filed: Dec. 29, 1976

[51] Int. Cl.² ............................................. A61B 10/00
[52] U.S. Cl. ..................................... 128/2 R; 128/1.3
[58] Field of Search ................. 128/1.3, 1.4, 1.5, 2 N, 128/2 R, 2 S, 2.1 E, 2.1 R, 2.1 Z, 2.1 M

[56] References Cited

U.S. PATENT DOCUMENTS

| | | | |
|---|---|---|---|
| 2,897,411 | 7/1959 | Brown et al. | 128/1.4 X |
| 3,468,302 | 9/1969 | Cowell | 128/2.1 R |
| 3,841,305 | 10/1974 | Hallgren | 128/1.3 |

OTHER PUBLICATIONS

Alexander, "American Journal of Medical Electronics," Jul.–Sep., 1962, pp. 181–187.

Primary Examiner—William E. Kamm
Attorney, Agent, or Firm—Sixbey, Friedman & Leedom

[57] ABSTRACT

A method of conducting a screening diagnostic examination to identify damaged, diseased, abnormal and/or malfunctioning parts of the body in humans or animals involves scanning the body with either the north or south magnetic pole of a magnet by applying the magnetic pole to the various body parts and observing the physical manifestations of the bioelectrical interaction between the scanned parts of the body and the applied magnetic field. Preferably, the magnetic pole strength at the examined body part is in the range 500–1500 gauss.

14 Claims, 9 Drawing Figures

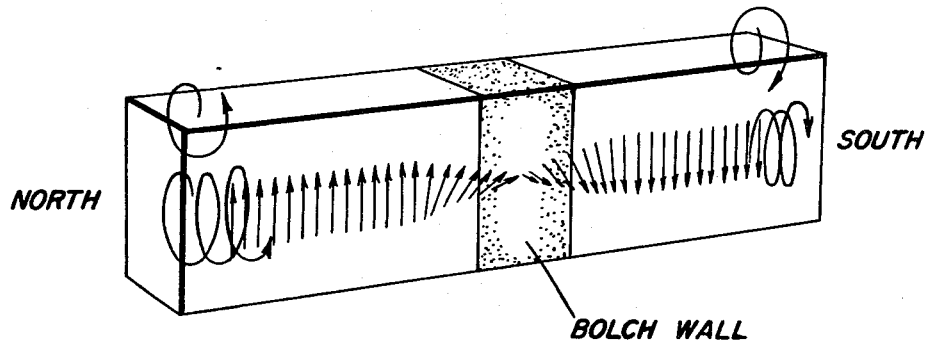
Fig. 1
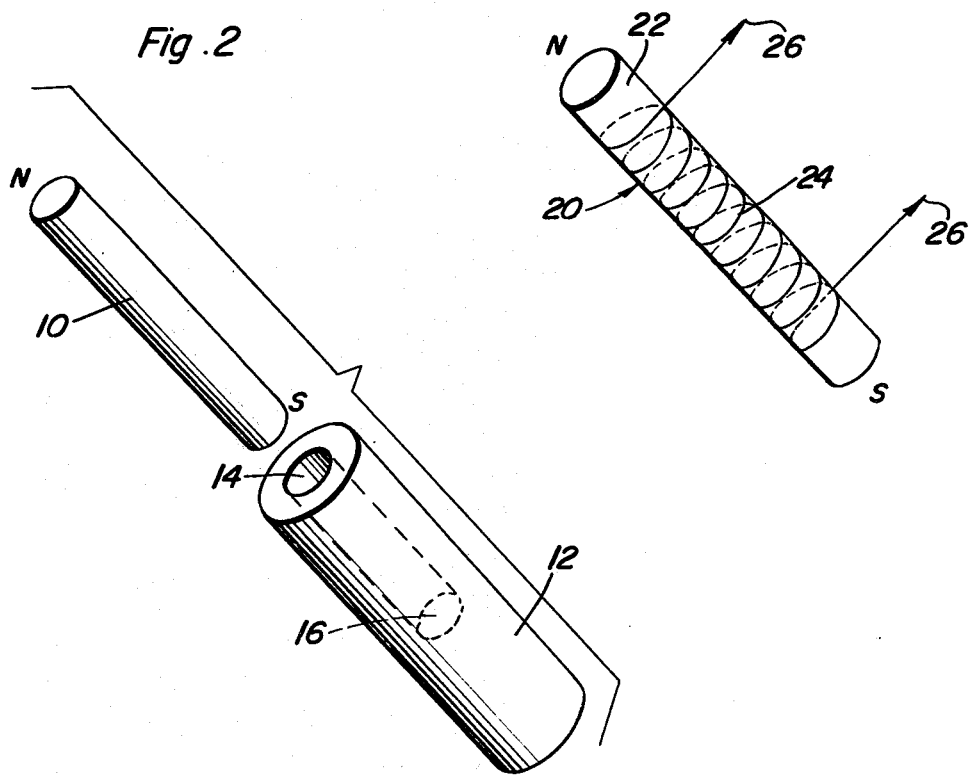
Fig. 2
Fig. 3

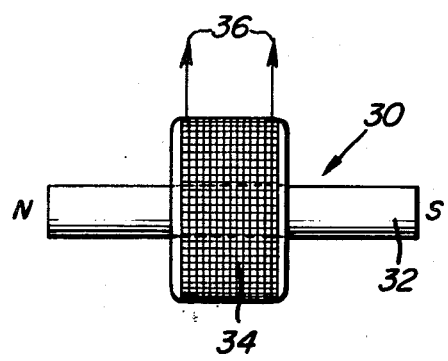
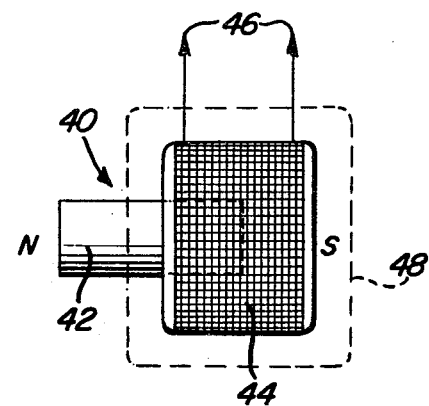
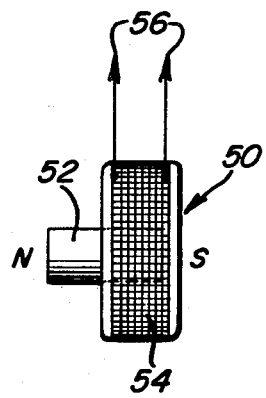
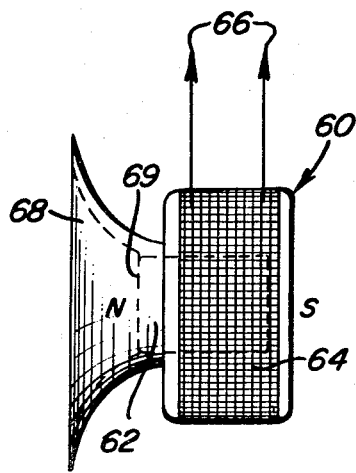
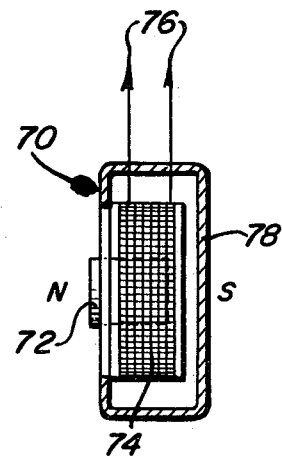

METHOD OF USING MAGNETIC FIELDS TO CONDUCT A SCREENING DIAGNOSTIC EXAMINATION

The present invention relates to magnetic energy, and, more particularly, to the application of such energy to human and animal biological systems as an aid in diagnosing malfunctioning parts of the systems.

The common belief over the years relating to magnets has been that the two magnetic poles, north and south, are homogeneous and that they emanate the same potential type of energy. This belief has now been found to be a misconception—the two poles of a magnet are in fact totally different in effect—and the application of the respective poles to living systems has been found to produce quite different results.

The north pole (which is defined as the south-seeking pole) is now believed to provide a negative form of energy while the south pole (which is defined as the north-seeking pole) is believed to provide a positive form of energy. To support this discovery, it has been found that upon examination of the electron paths associated with the fields surrounding the respective poles (see FIG. 1) that the south pole end of a magnet provides a right hand spin of electrons, i.e., a clockwise rotation of electron movement, as contrasted with the north pole electron spin, which presents a left hand spin or counter-clock-wise rotation of its electron field. It has further been observed that the lines of magnetic energy leave the south pole to re-enter the magnet at the Bloch Wall where the 180° phase change takes place, then leave the Bloch Wall at that point to go on as the north pole energy to re-enter the magnet at its north pole.

The present invention is primarily concerned with the use of magneto magnetic energy, i.e., magnetic energy derived from a magnet as opposed to some other source, on biological living systems. To understand the biological effects of the emissions of the magnetic poles, it should be appreciated that cells, blood cells, nerve and tissue cells and fluids are all bioelectric in nature and in operation and behavior. This can readily be demonstrated in its most simplistic form by taking a sample of whole blood from any animal, spinning off the fluids and placing a few drops of the red cells on a microscope slide. Upon microscopic examination it is evident that the cells are disoriented and unaligned, i.e., they appear to be arbitrarily arranged relative to one another. If one end of a cylinder magnet is slowly brought up under the microscope slide, it can be observed that the blood cells spin around and orient themselves according to the magnetic spin imparted to the red blood sample under examination. Application of the magnetic south pole to the slide imparts a right-hand spin to the sample, the blood cells spinning and becoming polarized in a clockwise direction. On the other hand, application of the magnetic north pole to the sample in a similar manner imparts a left-hand or counter-clockwise spin and polarization to the blood cells. Due to the different orientations of the blood cells and of the iron ions therein caused by application of the respective magnetic poles, the blood cells have been found to increase certain biological effects when exposed to the northpole and to increase other biological effects when exposed to the magnetic south pole. This same type of reaction has been noted in connection with the other type cells of the body, it having been observed and established that the application of north pole energies to an existing unhealthy or abnormal condition tends to cause an overall healing effect, akin to the body's own defense mechanism, while the application of south pole energies to such a condition tends to worsen the condition. A more detailed explanation of the biological effects of magnetic pole energies can be found in Davis et al., *Magnetism And Its Effects On The Living System*, Exposition Press, Inc. (1974) and Davis et al., *The Magnetic Effect*, Exposition Press, Inc. (1975). The effects of magnetic poles on non-biological matter is the subject of U.S. Pat. No. 3,947,533.

It is therefore the primary object of the present invention to utilize the bioelectrical interaction between human and animal biological systems and magnetic pole fields as the indicator in a screening diagnostic examination to identify diseased, abnormal, damaged and/or malfunctioning parts of the systems.

It is another object of the invention to provide a method of identifying parts of the human and animal systems which are properly functioning by scanning the systems with the north and/or south magnetic poles and observing the physical manifestation of the bioelectrical interaction between the scanned system and the pole energies.

It is still another object of the invention to provide a method for identifying malfunctioning parts of the human body by observing the tensioning (shortening) and relaxation (lengthening) of the legs in response to the application of the north and/or south magnetic poles to the body.

It is yet another object of this invention to provide magnetic apparatus having substantial pole separation, which apparatus are useful in the practice of the screening diagnostic examination of the present invention.

Other objects and advantages will become apparent from the following description taken in conjunction with the accompanying drawings.

FIG. 1 is a schematic representation of the electron paths around the north and south poles of a bar magnet.

FIG. 2 is an exploded perspective view of a permanent magnet and a housing therefor useful in the practice of the present invention.

FIG. 3 is a perspective view of a conventional electromagnet for use in the present invention.

FIG. 4 is a plan view of another electromagnet for use in the present invention.

FIG. 5 is a plan view of an electromagnet having shielded windings for use in the present invention.

FIG. 6 is a plan view of another electromagnet having shielded windings for use in the present invention.

FIG. 7 is a plan view of a small, flat electromagnet suitable for attachment to the body adjacent specified organs for use in accordance with the present invention.

FIG. 8 is a plan view of a small, flat electromagnet suitable for attachment to the body adjacent specified organs for use in accordance with the prevent invention.

Figure 9:
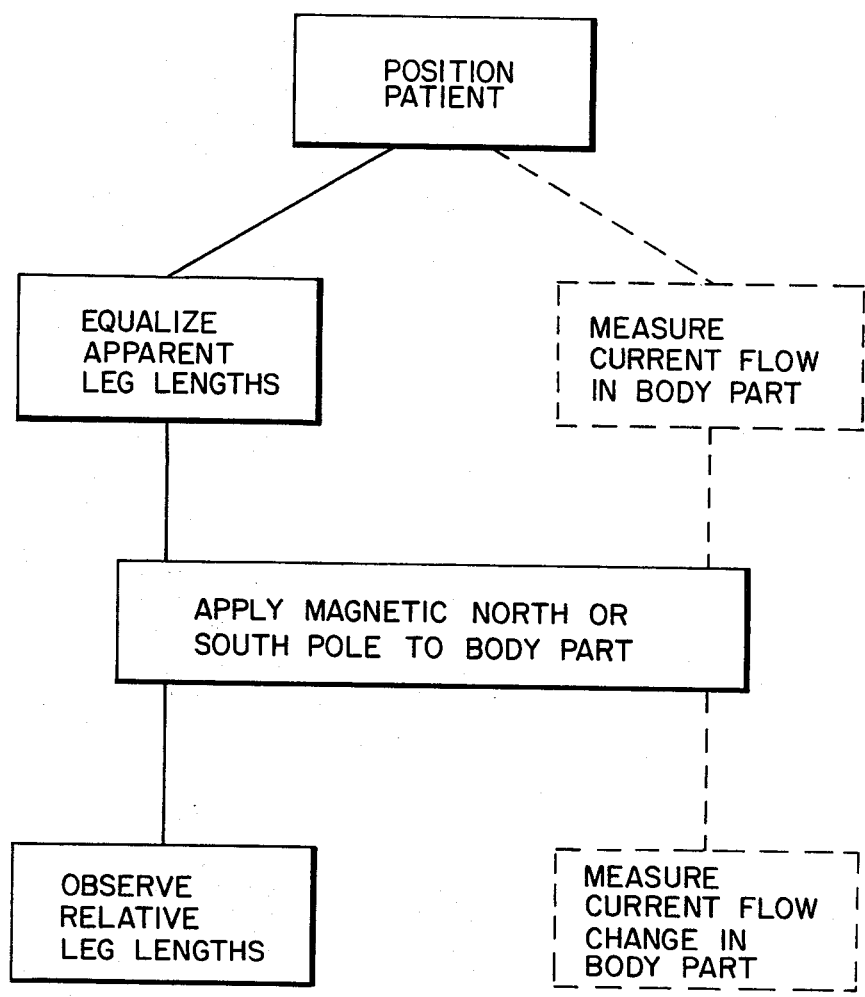
FIG. 9 is a block diagram outlining preferred forms of the method of the present invention.

In accordance with the aforesaid objects the present invention provides a diagnostic screening method for identifying damaged, diseased, abnormal and/or malfunctioning parts of the human and animal body. For ease of description the term "malfunctioning" will be used herein as generic to the various types of ailments, afflictions and conditions which may effect a part of the body by way of damage, disease, abnormality, and the like. It is not the purpose of the instant screening method to supplant in-depth conventional medical techniques for diagnosis of afflicted body parts—but rather to identify those body parts which are in need of in-depth diagnosis. There is a substantial need for a diagnostic screening method as furnished in accordance with the present invention. For example, such screening examinations are useful for rapid diagnosis in emergency or remote locations, at sea, under battlefield conditions, and the like, and have the dual advantage that:
(1) the person administering the test need not be a diagnostic physician, but may have only limited medical knowledge; and
(2) the administration of the test requires no electrical power and, therefore, is particularly appropriate for remote location and emergency condition situations.

In its broad form, the present invention pertains to the detection or identification of animal or human ailments, afflictions, abnormalitites, diseased or damaged body organs, glands, bones and other body parts. To practice the diagnostic screening examination, a single magnetic pole is applied to various parts of the body under examination, such as by scanning the body with the magnetic pole. When the proper pole of suitable strength is applied to a body part in which there exists some malfunction, as hereinbefore described, there is a bioelectrical interaction between the malfunctioning body part and the applied magnetic pole field. A physical manifestation of the interaction results which can be observed and utilized as an indicator of the existence of the malfunctioning body part at the magnetic pole location at the time the physical manifestation is observed. At the same time, the interaction causes a change in the flow of normal electrical body current, which change can be detected and measured by suitable electronic instrumentation attached to the body under examination. The magnitude of the measured voltages and/or currents is indicative of the existence and of the severity of the malfunction or abnormal condition when compared to the known normal voltage and/or current for the particular body part.

The physical manifestation of the bioelectrical interaction which is most readily observed is a tensioning or relaxation of the leg on the body side (i.e., left or right) corresponding to the location of the malfunctioning body part. The south pole of a magnet, when applied to any ailing or afflicted body part causes the appropriate leg to tension and to appear to shorten. On the other hand, the north pole of the magnet, when applied to an ailing or afflicted body part, causes, in the present procedure, a relaxation of the appropriate leg. At the same time, the leg appears to lengthen. Thus, for example, should there exist an infected or poorly operating right kidney, upon application of the south pole of a suitable magnet to the body adjacent the right kidney, there will be a contemporaneous physical reaction, an involuntary nerve response, manifested by a muscle pull and tensioning of the right leg. If the north pole of the same magnet is applied to the body adjacent the right kidney, there will be another involuntary nerve response, this time manifested by a contemporaneous relaxation of the right leg. The tensioning and relaxation of the right leg are readily observable and serve to provide valuable diagnostic information as to the existence of a defective body part. Without wishing to be bound to any particular theory, it is nevertheless believed that the observed responses can be explained when it is appreciated that the body's own bioelectrical supply system is sending negative energy to the malfunctioning right kidney.

When the south pole end of the magnet (positive energy) is applied to the right kidney, there is an involuntary automatic, reflex reaction of the nervous system to pull away from the applied positive energy, causing the observed tensioning. When the north pole of the magnet (negative energy is applied to the right kidney area, there is an arresting action as the negative body energy and the negative applied energy interact, causing the observed relaxation.

The observed tensioning and/or relaxation of the leg is accompanied by an observable, apparent shortening and/or lengthening of the leg. Thus, in addition to the muscle pull as an indicator of a malfunctioning body part, there is also the observable result that one leg appears to become longer than the other. While no actual lengthening or shortening of the physical leg takes place, the muscles of the leg are caused by the nerveous system to tension or relax, giving the visual indication of a corresponding shortening (tensioning) or lengthening (relaxation) of one of the legs. In order to assure that the lengthening/shortening observation is an accurate indicator, it is recommended that each foot be physically lifted and leveled before and after, and the apparent lengths of the legs equalized before, the application of the respective magnetic pole energies. By lifting and leveling each foot before and after the magnetic pole is applied to each body part, the resulting difference in length can be readily and accurately seen. Leg length changes of from $\frac{1}{2}$-inch and greater have been consistently observed.

In order to conduct a diagnostic evaluation in accordance with the present invention, place the patient on his back on a table, couch, bed or floor, place a pillow or other soft material under the head for comfort and straighten out the legs. Next, lift each leg by the ankles and, without pulling on the legs, adjust the position of the feet so that both heels are even. Place the magnet adjacent to, with the appropriate pole directed at and preferably in contact with, the body part to be examined. For example, if the right kidney is to be examined, have the patient roll slightly onto his left side and place the magnet under the body and against the right kidney.

With the magnet in place, move to the patient's feet and gently lift both feet about 18-inches by placing a hand under each ankle, press feet together, and observe if there is any noticeable difference in the length of either leg. Lower the feet to the surface. If the length of the leg on the side the magnet has been placed, e.g., the right leg corresponding to the right kidney, is shorter than the other leg, and the south pole has been applied to the kidney, then the proper diagnosis is that the right kidney is malfunctioning. FIG. 9 generally outlines in diagrammatic fashion (solid lines), this method of practicing the invention.

Remove the magnet from its initial position (e.g., adjacent the right kidney); lift and adjust the position of the legs to again make them even; place the magnet in position adjacent another body part; and then again lift and observe the legs to determine whether there has been a length change. Repeat this procedure with all body parts of interest to obtain a complete diagnosis.

An alternative indicator of the bioelectrical interaction which takes place between the malfunctioning body part and the applied pole energy is the measurable change in voltages and currents in the electrical energy flowing in the legs. Thus, when suitable electrodes of bioelectrial sensitive electronic instrumentation, as is conventionally available and well known, are attached to each leg, and magneto magnetic energy is applied to a malfunctioning body part, there is an observable and measurable voltage and current increase or decrease from the normal electrical flow through the legs, which increase or decrease is attributable to the bioelectrical interaction which takes place. The dashed lines in FIG. 9 outline an alternative method of the present invention in which electrical current flow changes are monitored. The currents and voltages can be readily recorded to give an indication of the existence of a malfunctioning body part. To briefly expand on this alternative indicator, it should be appreciated that when the north or south pole magneto magnetic energies are applied to a body part, there is a bioelectrial interaction between the bioelectrical energy of the body at that location and the applied magnetic energy with a resultant flow of measurable current and voltage. When the body part is normal, i.e., not malfunctioning, the measured current and voltage can be considered the norm for that body part. It has been observed that the bioelectrical properties of each and every organ, gland and other body part differ from those of all other body parts—i.e., the bioelectrical properties are distinctive. It has also been observed that when an abnormal condition or malfunction exists there is a distortion of normal bioelectrical activity at the affected body part. This distortion is measurable by measuring the current and/or voltage flow resulting from the interaction of the body energy at the affected body part with the magneto magnetic energy of the applied pole. The magnitude of the measured flow in indicative of the severity of the abnormality. Thus, an increase in negative bioelectrical potential compared to the norm, is noted at the site of a bone fracture. As the bone heals, the magnitude of this negative potential decreases and returns to normal.

The bioelectrical interactions which take place are evident when sufficiently sensitive measurements are properly made. It has been found that proper measurements can be made by applying electrodes to the lower extremities of the body under examination and by utilizing conventional high gain, filtered, band pass amplifiers to record the bioelectrical changes in nerve and muscle voltages and currents which result from applying a magnetic pole to a body part. A useful readout may be obtained by the use of a meter display or a suitable strip recorder system. Inasmuch as the reflex reaction time to the applied magnetic energy is only a few microseconds, it is necessary and desirable when making diagnostic evaluations to use a delayed time readout system to provide an extension of the time base.

Both the north and south magnetic poles have been found to be effective in detecting malfunctioning body parts in human and animal systems when properly applied thereto. Application of the energy emanating from a magnetic pole does not necessarily mean contacting the body part, i.e., the organ, bone, etc., affected, although contact is desirable where practical, but rather implies placing the body part to be scanned in sufficiently close proximity to a known strength magnetic pole that the energy reaching the part can be ascertained by conventional calculational techniques. Generally, the closer the body part to the magnetic pole the lower the energy of the pole source need to be since magnetic energy at any point has been found to vary inversely with distance from the point to the magnetic source. However, since in most cases pole contact or substantial pole contact with the body part can be accomplished, the magnetic energy of the source can in such a case be considered to be approximately the magnetic energy applied to the system.

The magnetic energy applied, in each case, may depend upon a number of factors, including the size of the patient and the location of the body part to which the magnetic energy is to be applied. However, 300 to 10,000 gauss measured at the scanned body part has been observed to be the practical useful magnetic energy range. Above 10,000 gauss, magnetic saturation considerations affect the response. Below 300 gauss, there is generally insufficient stimulus to obtain a realiable response. Generally speaking, magnetic field energies at the body part in the range 500–1500 gauss is preferred and is suitable. For example, a 1200 gauss magnet can pass its north or south pole energies through about 15 to 18 inches of body mass, thus enabling the energy of such a magnet to reach virtually any body part in the average person (up to about 200 pounds) when the magnet is applied to either the front or the back of the body. A typical 1200 gauss permanent magnet, such as an Alnico Magnet No. 5, weighs less than 1½ pounds and is therefore easily carried. For large patients weighing more than about 200 pounds, it is recommended that a 2000 gauss magnet be used where it is desired to reach a body part deep within the body's mass. Such a magnet offers a 20-inch depth of penetration field. The duration of magnetic energy application depends, of course, upon the strength of the applied field. However, for magnetic pole energies within the disclosed range, the time of application is generally unimportant since the physical or electronic manifestation of a response to the applied field appears virtually instantaneously, i.e., within a few microseconds.

The following Examples are illustrative of the practice of the present invention:

EXAMPLE I

Patient was a white male, age 56, of average body weight. The south pole of a 1200 gauss cylinder magnet was applied to the right kidney area of the back in accordance with the procedure set forth hereinbefore. No change in leg length was observed. The magnet was moved to the left kidney area of the back. It was noted that there was an observable 1-inch apparent shortening of the left leg.

Conclusion — Left kidney is malfunctioning or diseased. Conventional medical follow-up testing confirmed the diagnosis.

EXAMPLE II

Patient was a negro male, age 16, of average body weight. The south pole of a 1200 gauss cylinder magnet was placed against the patient's left ear with no observable change in leg length. The south pole of the magnet was next placed against patient's right ear. There was an observable apparent shortening of the right leg of about 1-inch.

Conclusion — Right ear is diseased or damaged in some fashion. Conventional medical follow-up testing revealed a right inner ear infection.

EXAMPLE III

Patient was a white female, age 54, who was internally injured in an accident. The south pole of a 1200 gauss magnet was used to scan the patient's body. A ¾ inch apparent shortening of the right leg was observed when the magnet was placed in the area of the right kidney.

Conclusion — Right kidney is damaged or malfunctioning. Conventional medical follow-up testing revealed that the right kidney and the spleen had been damaged in the accident.

Any magnet can be used in which the poles are sufficiently separated that the energy of each pole can be isolated from the energy of the other pole and a selected pole individually applied to a particularly body part of a living system. Thus, separation of the poles is the prime requisite in selecting an appropriate magnet. Straight bar or cylindrical magnets provide maximum pole separation and are preferred. Either solid state or long-wound electromagnets are equally useful. FIGS. 2–8 are exemplary of some of the preferred magnets and magnet configurations for use in the diagnostic screening examination of the present invention.

Turning to the drawings, FIG. 2 illustrates a conventional cylindrical permanent magnet 10, such as an Alnico magnet, having north and south poles at opposite ends thereof. A cylindrical sleeve 12, which may be constructed of steel, iron or like material, is adapted to slidably receive magnet 10 in its central bore 14. In a preferred form, bore 14 is formed through only a portion of the length of sleeve 12 such that, when fully inserted, one end (pole) of magnet 10 abuts or seats on the bore base 16 with the other end (pole) projecting outwardly from the bore 14. In this manner, with the south pole of the magnet, for example, within sleeve 12, the energy of the south pole is substantially contained and the effective pole separation is enhanced. At the same time, the north pole energies can be applied to the body of an animal or human, without interference from the south pole energies, and the magnet and sleeve of FIG. 2 can function effectively, efficiently and selectively as a diagnostic screening tool in the process of the present invention. When it becomes desirable to scan using the south magnetic pole, magnet 10 can be removed from bore 14 and replaced therein with the north magnetic pole abutting or seated on bore base 16.

Conventional electromagnets 20 and 30, as shown in FIGS. 3 and 4, may also be utilized as the diagnostic screening tool in the process of the present invention. Electromagnets 20, 30, consist of a core 22, 32 of soft steel or other suitable material, and windings 24, 34 of suitable insulated wire around core 22, 32. When D.C. power is applied to ends 26, 36 of winding 24, 34, one end of the core becomes the north, and the other end of the core becomes the south, magnetic pole with the poles separated by the length of the core 22, 32. Electromagnet 30 differs from electromagnet 20 in that there are a larger number of windings 34 and the windings are confined to the central portion of core 32. The increased number of windings makes electromagnet 30 more powerful than electromagnet 20. In addition, the effective pole separation has been found to be improved utilizing the configuration of electromagnet 30.

A preferred embodiment of a diagnostic screening tool is illustrated in FIG. 5 wherein electromagnet 40 consists of core 42 having a large number of windings 44 surrounding the core at only one end thereof so that the other end of the core projects from the windings 44. The windings 44 are surrounded by metal shield 48, which may be formed of steel mesh, thin tinned steel, heavy cast steel, or other well known suitable shielding materials. When D.C. power is applied to the ends 46 of winding 44, the magnetic poles are developed at opposite ends of the core 42. However, one pole (the south pole as illustrated) is physically housed within the windings and shielding and can contribute little magnetic energy. The result is a magnetic tool which effecitvely provides the energies of a single pole, i.e., the pole projecting from the windings (the north pole as illustrated), for scanning the body parts of animals or humans. The further value of electromagnet 40 is that when it becomes desirable to utilize the south pole for scanning, it is only necessary to switch the positive and negative electric potentials applied to winding ends 46, whereupon the core end projecting from the windings becomes the south pole. This can be readily accomplished by installing a conventional double pole-double throw switch (not shown) between the windings and the D.C. power source. A similar electromagnet 50 depicted in FIG. 6 differs primarily in the extent to which core 52 is inserted into windings 54. By varying the length of core within the windings, the strength and pole selectivity of the electromagnet can be altered. As with electromagnet 40, by changing the positive and negative electric potentials applied to winding ends 56, the polarity of the projecting end of the core, the end applied against the body during scanning, can be changed.

In the practice of the detection process of the present invention, it is sometimes desirable, rather than to scan the body with a single magnetic pole, to affix individual magnets to various parts of the body (e.g., one each attached over the heart, each lung, each kidney, liver, spleen, etc.) and then to select the desired polarity for the pole adjacent the body and to operate each magnet individually to determine whether there is a malfunctioning body part adjacent the location of the operating magnet. Electromagnets 60 and 70 shown in FIGS. 7 and 8 are particularly valuable for this sort of application in that they are compact and semi-flat in design. The electromagnets include a core 62,72 having one end embedded within and surrounded by windings 64,74 and including D.C. power supply connections at the ends 66,76 of the windings, at which ends conventional DPDT switches can be installed for altering the effective polarity of the electromagnet. The electromagnets may be either unshielded (as in FIG. 7) or shielded (as in FIG. 8). One means of affixing the electromagnets to the body is by use of a suction cup 68, formed of a flexible material, such as rubber or plastic. The cup 68 may be attached to the electromagnet in any convenient manner provided that when the cup is pressed against the human or animal body, the projecting pole end 69 is held in place adjacent the body. Desirably, the end of cup 68 attached to the electomagnet surrounds the pole end 69, as illustrated. Alternative means of affixing the electromagnets to the body include the use of tape, straps, or the like. When affixed in this manner, the tape or straps (not shown) pass over and in contact with the exterior of the electromagnets, for example over shield 78 of electromagnet 70, and then are suitably pressed into contact with or strapped to the body.

While the present invention has been described with reference to particular embodiments thereof, it will be understood that numerous modifications may be made by those skilled in the art without actually departing from the scope of the invention. Accordingly, all modifications and equivalents may be resorted to which fall within the scope of the invention as claimed.

What is claimed:

1. A method of conducting a screening diagnostic examination to detect malfunctioning parts of a body comprising the steps of:

(a) applying to the body under examination a single polarity magnetic pole, said magnetic pole having a strength such that the unipolar magnetic energy at the body part under examination is in the range 300 to 10,000 gauss;

(b) observing for the existence of a predetermined physical manifestation of the intereaction between any malfunctioning body part and the applied unipolar magnetic energy, the existence of said physical manifestation indicating a malfunctioning body part at the site of the magnetic pole when said manifestation is observed.

2. A method, as claimed in claim 1, wherein said magnetic energy is in the range 500 to 1500 gauss.

3. A method, as claimed in claim 1, wherein said physical manifestation is a change in the electrical current flow in the body and including the step of sensing the change in current flow in the body.

4. A method, as claimed in claim 1, wherein said body is a human body and said physical manifestation is a change in the relative tension-relaxation in the leg most closely adjacent the malfunctioning body part.

5. A method, as claimed in claim 4, wherein said applied magnetic pole is said north pole and said change is an observable relaxation in said leg.

6. A method, as claimed in claim 4, wherein said applied magnetic pole is said south pole and said change in an observable tensioning in said leg.

7. A method, as claimed in claim 1, wherein said body is a human body and said physical manifestation is a change in the apparent length of the leg most closely adjacent the malfunctioning body part.

8. A method, as claimed in claim 7, wherein said applied magnetic pole is said north pole and said change is an observable increase in the apparent length of said leg.

9. A method, as claimed in claim 8, wherein said apparent length increases at least ¼-inch.

10. A method, as claimed in claim 5, wherein said applied magnetic pole is said south pole and said change in an observable decrease in the apparent length of said leg.

11. A method, as claimed in claim 10, wherein said apparent length decreases at least ¼-inch.

12. A method, as claimed in claim 5 wherein said magnetic energy is in the range 500 to 1500 gauss and further including the steps of positioning said body with the legs parallel and with the apparent leg lengths equal prior to applying said magnetic pole to said body and observing for the existence of an increase in the apparent length of a leg during the application of said magnetic pole to said body.

13. A method, as claimed in claim 1, wherein the north magnetic pole is applied to the body under examination.

14. A method, as claimed in claim 1, wherein the south magnetic pole is applied to the body under examination.

* * * * *